United States Patent [19]

Barrett

[11] Patent Number: 4,834,529

[45] Date of Patent: May 30, 1989

[54] APPARATUS AND METHOD FOR DETERMINING THE SYMMETRY OF A SURFACE

[76] Inventor: Graham D. Barrett, Unit 13, Sanderling Mews, 4 Perina Way, City Beach, Western Australia, Australia

[21] Appl. No.: 926,930

[22] Filed: Nov. 3, 1986

[51] Int. Cl.⁴ .................................................. A61B 3/10
[52] U.S. Cl. ...................................... 351/212; 351/211
[58] Field of Search ................ 351/205, 211, 212, 237

[56] References Cited

U.S. PATENT DOCUMENTS 4,355,871 10/1982 Nevyas et al. ...................... 351/13

Primary Examiner—Rodney B. Bovernick
Assistant Examiner—P. M. Dzierzynski
Attorney, Agent, or Firm—Dennison, Meserole, Pollack & Scheiner

[57] ABSTRACT

Disclosed is an apparatus and method for determining the symmetry of a light reflecting surface by superimposition and comparison of a first reflected image ("first image") upon the same image ("second image") which has been rotated, relative to the first image, in a common plane about a common axis; wherein such apparatus and method find preferred application in keratometers and keratometry.

2 Claims, 2 Drawing Sheets

APPARATUS AND METHOD FOR DETERMINING THE SYMMETRY OF A SURFACE

BACKGROUND OF INVENTION

This invention relates to an apparatus and a method of its utilization in determining the symmetry of a surface.

In a preferred embodiment, the invention relates to an apparatus and method for determining the symmetry of a light reflecting surface by superimposition and comparison of a first reflected image upon the same image ("second reflected image") which has been rotated in a common plane about a common axis relative to the first reflected image; wherein such apparatus and method find preferred application in keratometers and in the art of keratometry.

For purposes of background in the field of keratometry, the reflection of a symmetrical image, such as, a circle, upon a cornea will be distorted to an eliptical image if the surface examined is not truly spherical. The distortion is a consequence of an astigmatism. However, it really is quite impossible, or at least not reproducible, to judge the nature of the astigmatism by viewing the reflected image, per se. But, if the departure from circular symmetry is read against a reference, information describing the astigmatic surface can be obtained. One of the most telling techniques involving the use of a reference is to compare the reflected circular image with itself, albeit rotated 90° and, ideally, superimposed upon the first reflected image. If the cornea section under view is astigmatic, the image of the circular light source will be eliptical and by superimposition of a second image which has been rotated 90° relative to the first image upon the first image, the respective lesser and major axes of the resulting ellipses will be orthogonal, and the observable departure from circularity is easily detected and quantitative measurement of the corneal defect is possible.

Keratometry is routinely employed to diagnose and define corneal astigmatism and to define corrective lenses, but is also employed during eye surgery—particularly during final suturing to minimize already existing or potentially induced astigmatism by local suture adjustment.

Conventional keratometers, however, are expensive, awkward to use, and consequently, their potential usefulness during surgery has never been realized.

U.S. Pat. No. 4,355,871 issued Oct. 16, 1982, to Nevyas and Traub is generally representative of prior art which recognizes the basic approach as described above relative to keratometers in keratometry; and is specifically representative of the technology relative to rotation and superimposition of eliptical image to detect astigmatism. However, there are practical limitations in the operation of devices such as that described in the '871 patent which limit their usefulness. These limitations relate to the complexity and the number of optical elements required to transform the image and read its information relating to symmetry. For example, the use of optical elements such as multiple beam splitting devices significantly decreases the light intensity ultimately made available to the observer and a functional dependence of the position of the optical device, i.e., its orientation about the axis of observation, on the degree of rotation of the second reflected image limits the utility of prior art devices such as those described in the '871 patent. Nevertheless, for purposes of the present disclosure, said U.S. Pat. No. 4,355,871 is fully incorporated herein by reference to the extent that it provides a fully enabling description of keratometric methods and devices which depend upon the reflection of a symmetrical target, such as a circular pattern, upon the cornea and the transmission of the reflected image to a point of convenient observation, such as, the ocular of a microscope in the surgical theater; wherein said image has superimposed the identical image which has been rotated, relative to the first image, a preferred angle of 90 degrees. Such a visual comparison of the two images gives an immediate qualitative interpretation of the lack of spherical symmetry of the cornea. This information can be interpreted quantitatively as well by the use of reading instruments which compare the reflected images against measuring grids, for example. Relative to the apparatus and method described in the '871 patent, it is further noted that such relevant prior art devices are further complicated by the requirement that optical elements account for any path length differences experienced by the primary image light ray family relative to the distance traversed by the secondary light ray family of the reflected, rotated image. Additionally, it is noted that such prior art devices are plagued with a left-right image reversal which requires user accommodation; although the prior art teaches that such limitations can be avoided, such limitations are avoided only at the expense of additional intensity losses and the addition of further elements to the already complicated system.

Thus, while the present invention will, for convenience of dislcosure, be recognized as an improvement over the prior art device exemplified in the fully incorporated by reference '871 patent, the present invention relies on a novel optical system which comprises only three elements for the desired comparison of a first and a second reflected image wherein the second image has been rotated 90 degrees and superimposed on said first image. Besides simplicity, robustness, and advantages of cost and maintenance, the optical system of the present invention is further distinguished over the prior art in the following ways: 1.) The optical system achieves the desired 90 degree rotation independently of the rotational attitude of the reflecting surface or the instrument; 2.) The final composite image does not suffer from left to right reversal and there is no need for conscious adjustment toward equalization of the light path of the first image relative to the light path of the second image; 3.) Because of the reduced number of optical elements in the optical system, the two images are presented at fully one-half of their original intensity; this result is achieved, principally, by having a single beam splitting means which is commonly used by both light paths; and 4.) The optical system of the present invention is sized to be fitted into the body of conventional binocular microscopes without exceptional costs, modifications or compromise of other functions of the microscope.

DETAILED DESCRIPTION OF THE INVENTION

Figure 1:
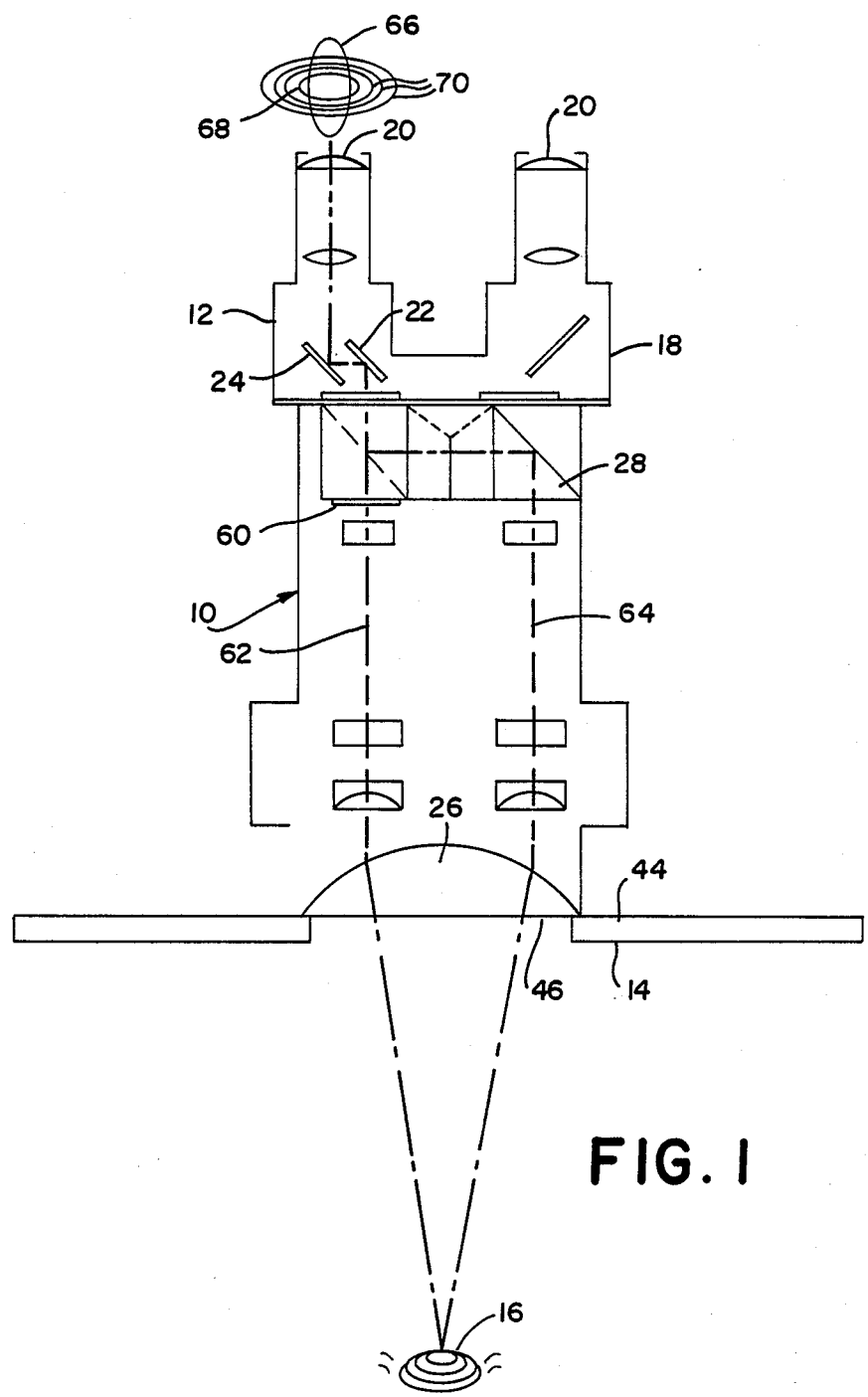
FIG. 1 is a schematic side elevation of a keratometer in accordance with the present invention.

The present invention will now be described, by way of example, with reference to the accompanying drawings. In FIG. 1 of the drawings, there is shown a keratometer 10 comprising a binocular microscope 12 and a light source 14 for projecting a circular trace upon a cornea 16.

The binocular microscope 12 comprises a detachable ocular assembly 18 which includes a pair of ocular lenses 20. The binocular microscope 12 also has an ocular objective lens 26.

Figure 2:
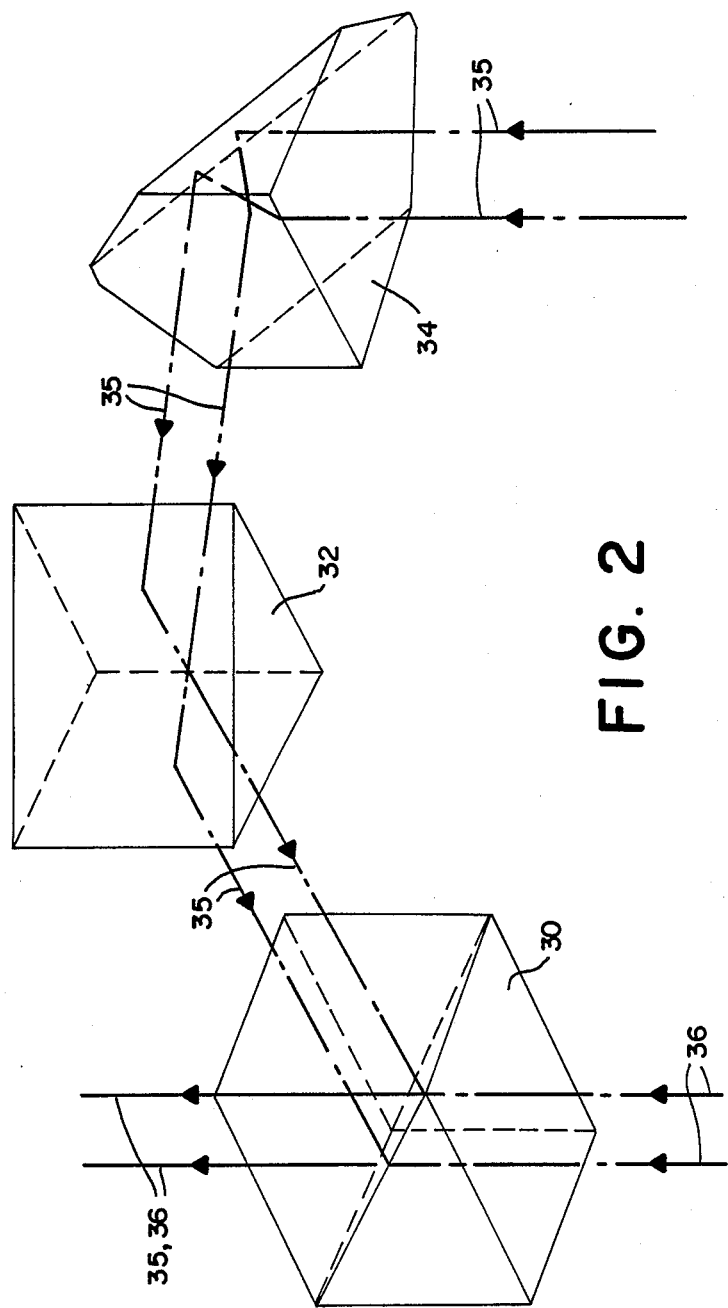
FIG. 2 is a schematic exploded view of an optical system of the keratometer of FIG. 1.

An optical device 28 is mounted in the binocular microscope 12 between the occular lens 20 and the objective lens 26. The optical device 28 is formed of three elements which can be seen more clearly in FIG. 2. The optical device 28 includes a cube beam splitter 30, a right angle prism 32 and a prism 34 containing two first order reflecting surfaces.

The device 10 of the present invention comprise three optical elements 30, 32 and 34. The arrangement of these optical elements is novel and provides a simultaneous 90 degree rotation and superimposition of the second image over the first image. These optical elements are: a beam splitter 30, preferably a cubed beam splitter, which is formed by cementing together the hypotenuse faces of two matched right angle glass prisms. Rays entering an optical face of the cube and striking the hypotenuse face will be divided into a transmitted and reflective component in a ratio which depends on the relative refractive indexes of the glass and cement. The reflection of the hypotenuse face can be enhanced by use of a thin metallic layer or by a dielectric interference film. A dichroic beam splitter could be utilized for color coding of the rotated and non-rotated images. The second optical element is a right angle prism 32 where the hypotenuse provides a first order mirror orientated at 45 degres to the optical face facing the reflective surface in the beam splitter. The third optical element is an Amici roof prism 34 and therefore contains two first order reflecting surfaces each aligned at 45 degrees to the remaining optical face of the right angle prism. Other prisms containing two first order reflecting surfaces such as a Penta prism could be used in place of the Amici roof prism. In operation as a keratometer 10, the light rays 35 from the corneal image of the circular light source 68 are deviated 90 degrees in a vetical plane and the image is inverted by the two reflecting surfaces in the Amici roof prism 34. The right angle prism 32 then deviates the light rays 35 a further 90 degrees in a horizontal plane to the reflecting surface of the beam splitter 30 and reverses the left/right orientation of the image. Fifty percent of the rays 35 reaching the beam splitting interface are deviated 90 degrees in the vertical plane and the left/right orientation of the image is reverted while the other 50 percent are transmitted through the partially reflecting interface. The final reflected image 35, 36 produced by the beam splitting device will have a 90 degree rotation in a clockwise direction from the original image and will be superimposed on the unrotated image transmitted by the beam splitting element. This prismatic arrangement has the advantage that 90 degree rotation of the primary image is achieved irrespective of the relative alignment of the axis of the image to the prismatic device. The light rays are processed in the parallel fashion rather than in a serial fashion and the superimposition is achieved simultaneously by the arrangement of the optical elements described.

The following disclosure is specifically directed to the: 1. Spatial relationship of the three optical elements of the device of the present invention when designed for use in keratometry in a binocular microscope 12; 2. A detailed account of the light pathways from light source to the observer, via, principally, the cornea 16, the objective lens system 26 of the microscope 12, the device of the present invention mounted within the body of the microscope 12, and the ocular 20 of the microscope 12; and 3. A detailed account of the light source and imaging;

1. Spatial Relationship of the Prismatic Elements

The spatial relationship of the individual optical elements 30, 32 and 34 used in the device 10 of the present invention is such that the optical centers of the beam splitter 30 and an Amici roof prism 34 coincide with the dual light pathways of the reflected corneal image within the body of the binocular microscope 12. The construction of the device is further simplified by choosing optical elements of such size that the three prismatic elements 30, 32 and 34 can be glued to one another with an optical adhesive such as Norland Optical Adhesive 60 which is cured by ultraviolet light. The three prismatic elements of the device are conveniently mounted on a stage within a housing 28 machined to be inserted in the body of the microscope at the point indicated above. The state carrying the optics can shift or rotate to remove the optics from the light pathways so that the microscope 12 can be used conventionally without physically removing the inserted housing 28. This greatly simplifies the construction and prevents any dust or other interference with the optical faces once they are glued together. It has been found that appropriate dimensions for the beam splitter 30 are 15×15 mm. Appropriate dimensions for the Amici roof prism 34 are 14×16×15 mm., and appropriate dimensions for the right angled prism 32 are 21×15×15 mm. With these dimensions the three optical elements 30, 32 and 34 match precisely and parallel faces can be glued together. Also, as mentioned above, with these dimensions the three optical elements can be placed in the light pathway of the microscope 12 such that the optical center of the beam splitter 30 coincides with one of the optical apertures of the microscope and the optical center of the Amici roof prism coincides with the center of the remaining optical aperture of the microscope. The optical elements 30, 32 and 32 are placed between the detachable eye piece assembly and the body of a microscope 12 such a a Zeiss microscope. At this site the light rays are parallel 62, 64 and therefore will not interfere with the focal length of the image. Therefore, even if the two light pathways 62, 64 of the device are not identical, both the rotated and unrotated images will be in focus when finally viewed by the eye piece assembly of the microscope. A difference in length between the two light pathways 62, 64 may result in the size of the image produced by the longer pathway being slightly smaller than the image produced by the more -direct route. With the present invention, however, the rotation of one of the images is produced simultaneously while the light rays 62, 64 are being directed to and recombined at the beam splitter 30. The light path of the rotated image therefore has a very direct route and the size of the rotated and unrotated images are almost identical. Therefore no path lengthening is necessary in the pathway of the unrotated image further simplifying the construction of the device. Although de minimis, any path difference could be corrected by conventional means; in fact, the three otherwise individual prismatic elements 30, 32 and 34 of the device could be manufactured as a single piece, and any path length corrections taken into consideration of the integral design.

2. Account of Light Pathway from Light Source to Cornea to Observer

As previously noted, a circular target is imaged on the cornea 16. The source and its configuration and integration with the microscope 12 can be considered conventional for the purpose of this disclosure and further to this purpose reference to the pertinent disclosure of the incorporated-by-reference U.S. Pat. No. 4,355,871 is made.

The surface of the cornea 16 acts as a convex relfector and the image produced is observed by the microscope. When the microscope is focused on the cornea, the cornea is position at the focal length of the objective lens 26 of the microscope. As a binocular device the microscope 12 has two independent light pathways 62, 64 which are focused on the same image, the corneal reflection of the circular light source 44. The objective lens 26 produces parallel light rays 62, 64 which are directed into each of the two light pathways and the respective optical apertures. In doing so the light rays can traverse varied lenses which are used to alter the magnification and focus of the lenses which are used to alter the magnifications and focus of the microscope. Most surgical microscopes have detachable ocular arrangements 18 such as includes mirrors 22 and 24 and therefore provide a suitable site for interfacing the keratometer device 28 of the present invention in each of the two light pathways. The device 28 is positioned such that the one light pathway 62 has a direct route 36 through the beam splitter 30 and therefore 50% of the light rays are transmitted unchanged. The Amici roof prism 34 is positioned in the other light pathway 64 and redirects the light rays 35 via the right angle prism 32 to the beam splitter 30 where the two light pathways 62, 64 are recombined as light beams 35–36. The 90° image rotation of light beam 35 is achieved simultaneously while the light rays are being redirected through the Amici roof prism 34, right angled prism 32 and recombined at the beam splitter 30. One of the oculars 20 of the microscope 12 acts as a telescope and images both the rotated and unrotated images 62, 67.

3. Light Source and Technique for Quantitative Estimation of Astigmatism

A preferred light source 14 or target used in the keratometer device 10 embodiment of the present invention consists of multiple illuminated rings 54 preferably by a fiberoptic mechanism.

The light source 14 projects a circular light image on to the cornea 16. In use, the binocular microscope 12 is focused on the cornea 16 in known manner. The image of the light source 14 is reflected from the cornea 15 and viewed through the objective lens 26. A first portion 62 of the reflected image passes through the optical device 28 without being rotated at all and then is reflected by the mirrors 22 and 24 to appear at the ocular lens 20. However, this first portion also passes through the red filter 60 which filters out the part of the reflected image.

A second portion 64 of the reflected image passes through the optical device 28 to the right as shown in FIG. 1. Thus, it passes through the Amici roof prism 34, the right angle prism 32 and the cube beam splitter 30 in turn such that the image is rotated through 90°. The cube beam splitter 30 superimposes the reflected image of the second portion 64 on the reflected image of the first portion 62 as described hereinabove. Thus, the reflected second portion 64 is also reflected by the mirrors 22 and 24 and appears at the ocular lens 20.

Although the filter 60 has been shown in the path of the non-rotated optical image in FIG. 1, it could equally well be placed alternatively in the path of the rotated optical image.

A preferred arrangement of a circular target consists of four illuminated rings distinguished by a color coding mechanism such that the inner ring 68 is a white light source and the three outer rings 70 are a green light source. The multiple concentric green rings 70 and central white ring 68, when used in conjunction with a complementary red filter 60 in one of the light pathways 62 (preferable that of the rotated image), provides a quantitative estimation of the amount of overlap of the superimposed images, which will be eliptical in the event the cornea 16 is not symmetrical about the chosen optical axis. The unrotated image of the multiple rings will consist of an innermost white ring 68 with three concentric outer green rigns 70. In contrast the 90° rotated image will be limited to an image of the innermost white ring 68 which will appear red, see 66. When the unrotated and rotated images are superimposed the amount of overlap of the red ring 66 can be reproducibly read by observing the extent the red ring 66 overlaps the inner white ring 68 and multiple concentric outer green rings 70. Other complementary colors besides green and red could be used in either light pathways. Furthermore a dichroic beam splitter could also be used to allow the selective transmission and screening of the different color light sources in the same manner as a colored filter 60. The superimposition of a 90° rotated circular image on an unrotated image of itself requires that the image be concentric to the imaging device. If the image is not centered then the rotated and unrotated images will not be concentric. Therefore a central point light source is provided as part of the light source 14 to facilitate the correct concentric alignment of the rotated and unrotated images. That is, the reflected images of the cenral point are coincident on achieving correct concentric alignment. The position of the rotated 62 and non rotated 64 images are adjusted so that they overlap in a concentric fashion by manually adjusting the position of the microscope 12 or using the electromechanical X-Y control of the microscope 12. As mentioned, the preferred targeting device (i.e., light source 14) is a fiberoptic device as this allows the presentation of extremely bright and narrow illuminated rings 66, 68 and 70. Furthermore the use of a fiberoptic illuminating target is safer as no electrical connection is required to the illuminating target. The multiple illuminated rings 66, 68 and 70 can be supplied by a single bulb such as a halogen bulb in the fiberoptic light source and therefore replacement and maintenance of the device in the event of breakdown can be rapidly and economically achieved. The absence of heat buildup in the microscope is also a distinct advantage of a remote light source. It is also envisioned that the fiberoptic illuminated target can use the integral light source of the microscope as its own light source by a simple modification (not shown) to the housing of the microscope light bulb. This would further reduce the cost of the keratometer 10 which would not require any external connections either electrical or fiberoptic.

What is claimed is:

1. In a keratometer comprising: a binocular microscope; having an objective lens system and an ocular lens system, two independent light pathways, the objective lens being arranged to produce parallel light beams which are directed into respective light pathways of the binocular microscope; a light source for projecting a circular trace upon a cornea and an optical device mounted between the objective lens system and the ocular lens system of the binocular microscope for combiing the transmitted, reflected image of the light source with the same image rotated 90° about the common, central axis of symmetry; wherein said combination occurs in a common plane and in a position for viewing by one of the oculars of the binocular microscope; the improvement comprising the position and prismatic elements of said optical device, wherein a cube beam splitter; a right angle prism, and a prism containing two first order reflecting surfaces are positioned in the order listed and aligned to achieve the defined transformation upon said image.

2. The device of claim 1 wherein the prism containing two first order reflecting surfaces is an Amici roof prism.

* * * * *